(12) United States Patent
Precheur

(10) Patent No.: US 12,135,538 B2
(45) Date of Patent: Nov. 5, 2024

(54) INSTALLATION FOR THE THREE-DIMENSIONAL PRINTING OF A MEDICAL DEVICE

(71) Applicant: MED IN TOWN, Saint Chamond (FR)

(72) Inventor: Jérôme Precheur, Saint Chamond (FR)

(73) Assignee: MED IN TOWN, Saint Chamond (FR)

( * ) Notice: Subject to any disclaimer, the term of this patent is extended or adjusted under 35 U.S.C. 154(b) by 354 days.

(21) Appl. No.: 17/621,251

(22) PCT Filed: May 21, 2020

(86) PCT No.: PCT/FR2020/050854
§ 371 (c)(1),
(2) Date: Dec. 21, 2021

(87) PCT Pub. No.: WO2020/260781
PCT Pub. Date: Dec. 30, 2020

(65) Prior Publication Data
US 2022/0413463 A1    Dec. 29, 2022

(30) Foreign Application Priority Data
Jun. 24, 2019 (FR) ..................................... 1906770

(51) Int. Cl.
*G05B 19/4099* (2006.01)
(52) U.S. Cl.
CPC ............... *G05B 19/4099* (2013.01); *G05B 2219/49023* (2013.01)
(58) Field of Classification Search
CPC ...... G05B 19/4099; G05B 2219/49023; B29C 64/25; B29C 64/268; B29C 64/364; B29C 64/153; B29C 64/314; B29C 64/35; B29C 64/357; B29C 64/386; C12M 33/00; C12M 37/00; Y02P 10/25; B33Y 30/00; B33Y 50/00; B33Y 40/20
See application file for complete search history.

(56) References Cited

U.S. PATENT DOCUMENTS

| | | | |
|---|---|---|---|
| 2014/0277659 A1* | 9/2014 | Kumar | G05B 19/4097 700/117 |
| 2016/0010883 A1 | 1/2016 | Jornitz et al. | |
| 2019/0009334 A1* | 1/2019 | Effernelli | B33Y 10/00 |
| 2019/0061294 A1* | 2/2019 | Zong | B29D 11/00182 |

FOREIGN PATENT DOCUMENTS

| | | |
|---|---|---|
| CN | 106901770 | 6/2017 |
| FR | 3058338 | 5/2018 |
| WO | WO 2018/150231 | 8/2018 |

OTHER PUBLICATIONS

International Search Report and the Written Opinion Dated Oct. 8, 2020 From the International Searching Authority Re. Application No. PCT /FR2020/050854 and Its Translation of Search Report Into English. (13 Pages).

* cited by examiner

*Primary Examiner* — Charles R Kasenge

(57) ABSTRACT

The invention relates to an installation (1) for the three-dimensional printing of a medical device directly at a location where the medical device is to be used.
According to the invention, the installation comprises a container (2) comprising inside it:
  a production module (3) comprising a 3D printer (6);
  a clean room (4) comprising means (12) for washing and disinfection of the printed medical device, and a machine (13) for packaging the washed and disinfected medical device.

8 Claims, 2 Drawing Sheets

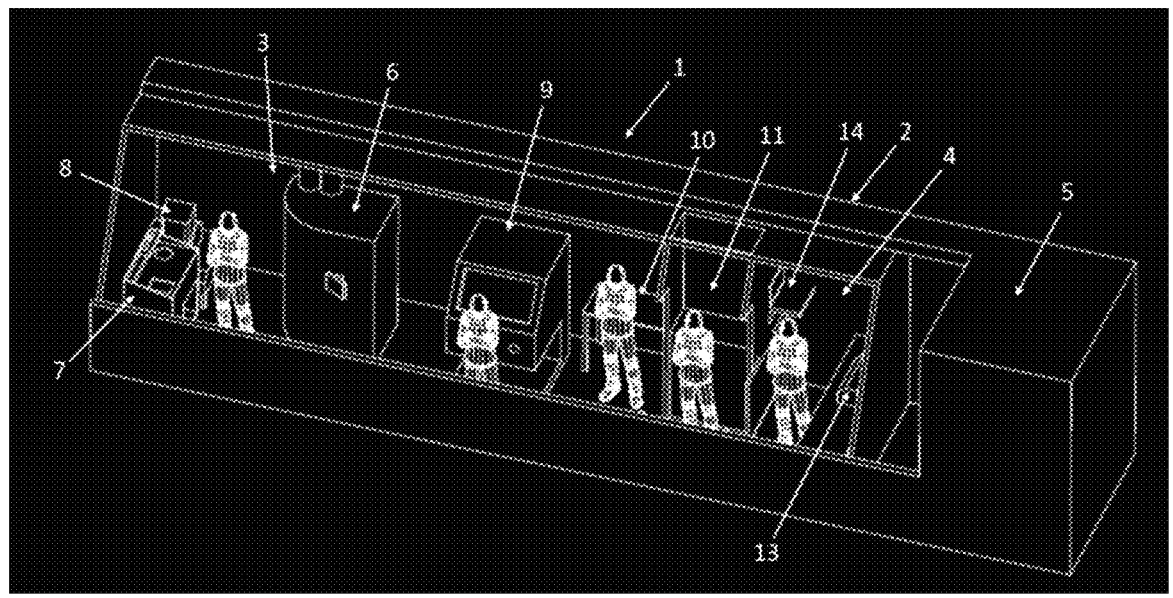
[Fig. 1]
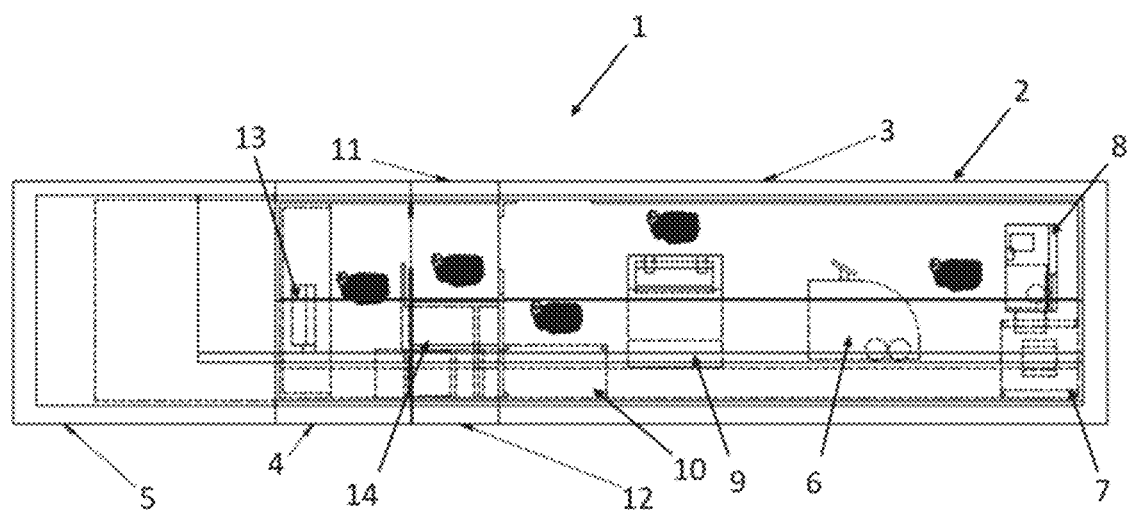
[Fig. 2]

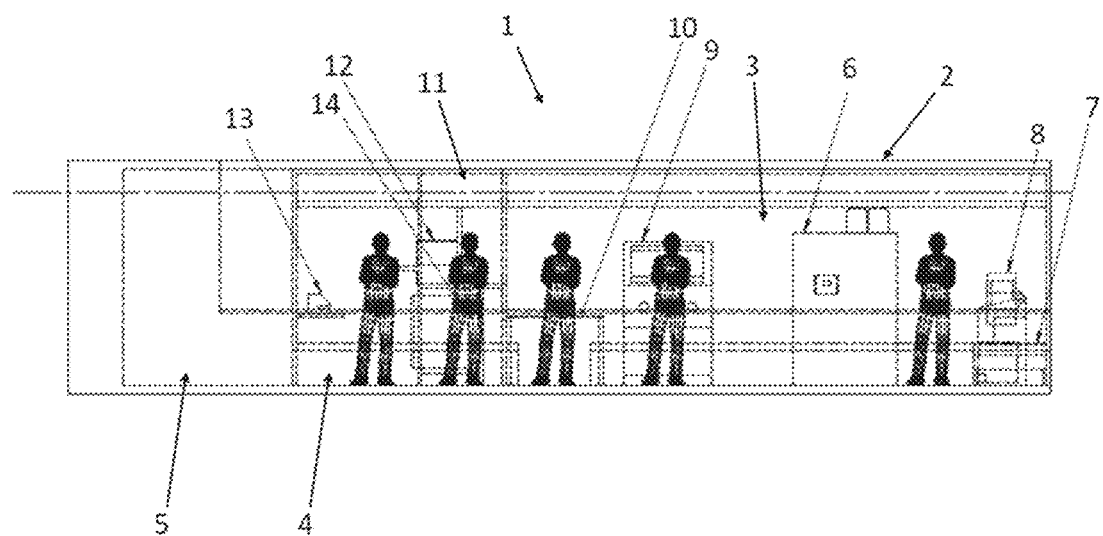
[Fig. 3]

INSTALLATION FOR THE THREE-DIMENSIONAL PRINTING OF A MEDICAL DEVICE

RELATED APPLICATIONS

This application is a National Phase of PCT Patent Application No. PCT/FR2020/050854 having International filing date of May 22, 2020, which claims the benefit of priority of French Patent Application No. FR1906770 filed on Jun. 24, 2019. The contents of the above applications are all incorporated by reference as if fully set forth herein in their entirety.

FIELD AND BACKGROUND OF THE INVENTION

The invention relates to the technical field of manufacturing medical devices, i.e. any instrument, apparatus or equipment, used for the diagnosis, the prevention or the treatment of a disease, an injury or a disability, or for performing a surgical operation.

The invention relates more specifically to a three-dimensional printing installation of such a medical device, directly at the location where it is to be used, for example in a hospital.

In the state of the art, hospitals must procure a considerable number of medical devices, i.e. instruments, ancillaries, trial implants, or any other element intended to be used for diagnosis, prevention, treatment of a disease, an injury, or a disability, or for performing a surgical operation.

The considerable number of these medical devices makes tracing and monitoring them complex, such that it sometimes occurs that one or more of these medical devices are not delivered on time, thus compromising the medical practice.

Moreover, a large portion of these medical devices are made of metal and requires after use, to be transported to be treated and refurbished, and delivered again to hospitals.

Monitoring and managing these different operations are therefore expensive and fastidious, and generate a risk for the end patient.

Moreover, for a hospital for example, the process of ordering a medical device is cumbersome and complex and requires a significant number of stakeholders and suppliers to intervene. The search for medical devices well-adapted to patients therefore becomes fastidious.

Moreover, orders are generally placed wholesale, which involves the management of a stock, with products identified and packaged in different ways according to the suppliers.

Certain hospitals have attempted to equip themselves with 3D printers, unsuccessfully, and with significant difficulties in understanding the total printing process until the end product is packaged.

Three-dimensional printing installations of a medical device directly at the location where the medical device is to be used are known from documents CN106901770 and US2016/010883, which have the disadvantage of being complex and expensive.

SUMMARY OF THE INVENTION

One of the aims of the invention is therefore to overcome the abovementioned problems by providing an installation making it possible to avoid the hazards linked to treatments and to the delivery of medical devices.

Another aim of the invention is to simplify the tracing and monitoring of said medical devices.

The invention also aims to decrease the cost and time for ordering and managing said medical devise, while making it possible to choose the medical devices which are the best suited to patients.

According to the invention, the installation comprises a container comprising inside it:
 a production module comprising a 3D printer;
 a clean room, separate from the production module, comprising means for washing and disinfecting the printed medical device, and a machine for packaging the washed and disinfected medical device.

From the above, the installation makes it possible to manufacture a medical device, within the same location where it is to be used, in a short supply chain, this removing the hazards linked to transportation. The manufacturing of the medical device is ensured in total transparency, under optimal conditions by allowing a hospital use, for example in an operating theatre. The clean room according to standard ISO 14644-1 comprises means for controlling the cleanliness of the air. These means comprise a filtration unit making it possible to control particle concentration and to avoid any microbial contamination inside the clean room. The parameters such as temperature, humidity and relative pressure are also controlled and maintained at a specific level.

The printed medical devices are all identified and packaged homogenously such that their tracing and monitoring are improved.

According to a particular embodiment, the 3D printer is a powder selective laser sintering (SLS) machine, and the production module comprises a station for unpackaging a printed medical device, and a station for de-powdering an unpackaged medical device.

Advantageously, the production module also comprises a powder mixer, making it possible to prepare directly in the container, a powder of materials to be printed, coming for example from a recycling operation.

The de-powdering is performed by any suitable technique. For example, the de-powdering station comprises a sandblasting de-powdering device.

Advantageously, the production module comprises a control and rework station for the printed medical device.

According to a particular embodiment, the clean room comprises a sterilisation device, preferably of the autoclave type.

Preferably, the production module communicates with the clean room by way of an airlock.

According to a particular embodiment, the 3D printer is controlled by a man-machine interface configured to allow a user to select a medical device to be printed, accessible from a database.

DESCRIPTION OF THE SEVERAL VIEWS OF THE DRAWINGS

FIG. 1 is a schematic representation illustrating, in perspective, the installation according to the invention;

FIG. 2 is a schematic representation of the installation of FIG. 1, as a top view;

FIG. 3 is a schematic representation of the installation of FIG. 1, as a front view.

DESCRIPTION OF SPECIFIC EMBODIMENTS OF THE INVENTION

In reference to FIGS. 1 to 3, the invention relates to an installation (1) for three-dimensionally printing a medical device, comprising a container (2) adapted to be positioned directly at the location where the medical device is to be used, for example in a hospital.

The invention thus makes it possible to print medical devices directly onsite, and to avoid the hazards of the treatment and of the transportation of these devices, while guaranteeing a hospital use, for example in an operating theatre.

To this end, the container (2) comprises inside it a production module (3), a clean room (4) separate from the production module, and preferably a machine room (5).

The production module (3) comprises at least one 3D printer (6), preferably of the powder sintering (SLS) machine.

The production module (3) can be configured to make it possible to work with a recycled powder to supply the 3D printer (6). To this end, the production module (3) advantageously comprises a (possibly recycled) powder mixer (7), to prepare the powder before filling in the 3D printer (6). The powder used is recyclable, for example made of polyamide.

The production module (3) then comprises a station for unpackaging (8) the three-dimensional printed medical device. The unpackaging station (8) makes it possible to unpackage the printed raw medical device, in view of it being de-powdered. The production module (3) also comprises a station for de-powdering (9) the unpackaged medical device, comprising for example, a sandblasting de-powdering device.

Advantageously, the unpackaging station (8) is adjacent to the mixer (7), such that the powder coming from the unpackaging is directly forwarded into the mixer (7) in view of it being reused in the 3D printer (6).

The production module (3) advantageously comprises a control and rework station (10) for the de-powdered medical device, for example by means of conventional equipment of the calliper or other type and/or by means of reverse engineering by 3D scanner.

The production module (3) communicates with the clean room (4) by way of an airlock (11). The clean room (4) comprises means (13) for washing and disinfecting the de-powdered medical device, in particular a disinfecting washer, and a machine (13), in particular under vacuum, for packaging the washed and disinfected medical device. The clean room (4) comprises means for controlling the cleanliness of the air, for example in the form of a filtration unit, making it possible to control the particle concentration and to avoid any microbial contamination inside the clean room (4).

The clean room (4) also preferably comprises a sterilisation device (14), of the autoclave type, to sterilise the packaged medical device. The packaged and sterilised device is then possibly over-packaged, for example in a specific cardboard box at an over-packaging station (not represented).

The packaging and the over-packaging are standard at the location where the medical device is used, for example at the hospital, and have the identifications necessary for ensuring the tracing and monitoring of the medical device.

The machine room (5) of the container (2) makes it possible for the treatment of the air of the container (2), the production of water, compressed air, and the management of the electric powering of different equipment, as well as possible alarms.

Preferably, the container (2) comprises means for collecting (not represented) printed medical devices to be discarded, in particular which are not compliant or which are already used, in view of them being recycled.

The 3D printer (6) of the production module (3) is preferably controlled by a man-machine interface configured to make it possible for a user to select a medical device to be printed, accessible from a database.

For example, the user can correspond to a pharmacist, an operating theatre manager, a surgeon, a teacher or any other person.

On this man-machine interface, the user can select the medical device to be printed which is the most suitable for the patient by performing research, for example by criteria, by manufacturers or also by manufacturing history. Medical devices to be printed can be displayed in the form of a drop-down menu with a three-dimensional image of each medical device, as well as a technical description. For example, the technical description comprises technical characteristics and the price of each medical device.

To obtain this display for the user, the man-machine interface is connected to a file server integrating an electronic document management module. This electronic document management module preferably integrates the technical description and the three-dimensional manufacturing plan of each medical device.

The three-dimensional manufacturing plan of each medical device can be stored in various formats. Preferably, the manufacturing plan is stored in STL format which is used in stereolithographic software and which has been developed by the company 3D Systems®.

Complementarily or alternatively, the electronic document management module can accept PDF- or video-type files. In addition, the electronic document management module can be configured to display treatments on the manufacturing plans, in order to standardise them or obtain information from them, such as dimension information, in order to present them to the user or to make it possible for targeted research according to criteria provided by the user in the man-machine interface.

The database is preferably supplied directly by manufacturers of medical devices. To do this, manufacturers of medical devices have means for securely connecting to the database, in order to file the three-dimensional manufacturing plans.

To guarantee the property of the digital files of the manufacturer, the database can be configured to automatically encrypt the manufacturing plans received, in order that they cannot be recovered by the user, but only used by the 3D printer (6) when the user selects them.

In a variant, the manufacturing plans corresponding to the medical devices to be printed can be stored only on a server of the manufacturer of medical devices and accessible only when the user launches the print command. Thus, in this embodiment, the 3D printer (6) comprises means for remotely connecting to the server of each manufacturer and for having access to the manufacturing plans of the medical device selected by the user.

Preferably, the manufacturing plans are stored in the encrypted database, accessible by the electronic document management module, in order to overcome any network malfunctioning to control the 3D printer (6).

Different access rights can be implemented to restrict access to the information contained in this database. For example, the manufacturers can have the right to modify the prices and the plans of each of their medical devices. For all that, a particular medical device manufacturer has not access to the plans, nor eve to the previewing elements of a medical device of another manufacturer. Furthermore, a medical device can be implanted in the body of a patient by means of an implanting instrument. To facilitate the fulfilment or the selection of implanting instruments of the medical device selected by the user, implanting instrument manufacturers can also have access to all or some of the information from the database.

Likewise, hospitals are often managed by buyers or financial departments, the main concern of which is to streamline the operating costs of a hospital. These financial departments can also have access to certain technical information of the medical devices proposed by the manufacturers in order to define strategies for purchasing certain medical devices according to the cost or the commercial relationship established with a specific manufacturer.

Complementarily to these conventional actors of the hospital and the supply of implanting instruments or medical devices, a user for managing multiple three-dimensional printing installations (1) can also have access to certain information contained in this database in order to be able to produce statistics on the use of one or more medical devices according to research carried out by the user on the man-machine interface.

This information analysis makes it possible to improve the user experience in presenting information on the man-machine interface in order to recommend the devices which are the most often used by users and, thus, the reduce the selection time of the devices most commonly used.

The management user can also intervene on the database to access all of the profiles of the manufacturers, users or financial departments in order to restrict or to increase their right of access to different information contained in the database according to specific constraints.

Thus, in addition to the electronic document management module, the server preferably comprises a securing module making it possible for a secure access control to different stakeholders according to their access right. This securing module also comprises means for encrypting manufacturing plans and digital signature means making it possible to trace and legalise a production request of a user. The server can also comprise a statistical module in order to facilitate the analysis of the management user.

This server can be integrated into a global information system making it possible to control each step of the manufacturing method and to verify the compliance of the parts manufactured by the 3D printer (6) by using the manufacturing plans stored in the database.

From the above, the end user, such as a surgeon for example, can consult freely, in the database, the files of the medical devices to be printed, as well as their associated documentation.

Thus, after having chosen the medical device which is the best suited to the patient, the user selects the quantity, and possibly the delivery address internally in the location where the container (2) is located, for example, the orthopaedics department, etc.

The cycle can then start in the production module (3) by a step of preparing and mixing the powder, possibly recycled.

The 3D printer (6) is then prepared and launched for the selective laser sintering printing of the powder. Once the printing has ended, the printed medical device is unpackaged from a powder unit coming from the 3D printer (6). The superfluous powder is thus reintegrated in the mixer (7).

The unpackaged medical device is then channeled to the de-powdering station (9) to remove all the powder residue, preferably by sandblasting. It can also be necessary to make the medical device undergo a tribofinishing operation to obtain an optimal surface state.

Once de-powdered, the medical device can be pre-washed and is then sent to the control and rework station (10).

If the medical device does not meet expectations, it is refused, and for example, discarded in collection means in view of it being recycled.

If it meets expectations, it is delivered to the clean room (4), passing through the airlock (11). The medical device is washed and disinfected in the washing and disinfection means (12), then packaged. The packaged medical device is then sterilised in an autoclave, possibly located in the clean room (4).

The product is then over-packaged and is stored, awaiting delivery. The product is then forwarded, in particular into the room of the hospital where medical practice is to be carried out.

From the above, the installation (1) according to the invention makes it possible to avoid the hazards linked to the treatments and to the delivery of the medical devices, since these are manufactured directly onsite, on request. Medical devices are packaged and identified according to the standards of the location in which the container (2) is installed, which makes it possible to simplify the tracing and the monitoring of said medical devices.

The database, accessible through the man-machine interface makes it possible for the user to interact with one single stakeholder while having access to a plurality of medical devices of different manufacturers. The cost and the time for controlling and managing said medical devices are decreased.

What is claimed is:

1. A three-dimensional printing installation of a medical device directly at a location where the medical device is to be used, wherein the installation comprises a container containing therein:
   a production module comprising a 3D printer;
   a clean room, separate from the production module, comprising means for washing and disinfecting the printed medical device, and a machine for packaging the washed and disinfected medical device;
   wherein the 3D printer is a powder selective laser sintering machine, and the production module comprises a station for unpackaging a printed medical device, and a station for de-powdering an unpackaged medical device.

2. The installation according to claim 1, wherein the production module comprises a powder mixer.

3. The installation according to claim 1, wherein the de-powdering station comprises a sandblasting de-powdering device.

4. The installation according to claim 1, wherein the production module comprises a control and rework station for the printed medical device.

5. The installation according to claim 1, wherein the clean room comprises a sterilisation device.

6. The installation according to claim 1, wherein the production module communicates with the clean room by way of an airlock.

7. The installation according to claim 1, wherein the 3D printer is controlled by a man-machine interface configured to make it possible for a user to select a medical device to be printed, accessible from a database.

8. The installation according to claim 1, wherein the container comprises means for collecting printed medical devices to be discarded.

* * * * *